United States Patent [19]
Selinger

[11] Patent Number: 5,514,840
[45] Date of Patent: May 7, 1996

[54] STETHOSCOPE

[75] Inventor: Irwin Selinger, Old Westbury, N.Y.

[73] Assignee: Graham-Field, Inc., Hauppauge, N.Y.

[21] Appl. No.: 347,868

[22] Filed: Dec. 1, 1994

[51] Int. Cl.$^6$ .................................................. A61B 7/02
[52] U.S. Cl. ............................................ 181/131; 181/137
[58] Field of Search ...................................... 181/131, 137

[56] References Cited

U.S. PATENT DOCUMENTS

| | | | |
|---|---|---|---|
| 3,938,615 | 2/1976 | Bodenger | 181/131 |
| 4,776,426 | 10/1988 | Kazama | 181/131 |

*Primary Examiner*—Khanh Dang
*Attorney, Agent, or Firm*—Bauer & Schaffer

[57] ABSTRACT

A chesthead having a pair of acoustic chambers, each of which is provided with a diametrically arranged wall separating the acoustic chamber into two portions. The two portions in each chamber are connected selectively to a pair of sound tubes so that dual sounds from each chamber are fed to the user simultaneously.

3 Claims, 2 Drawing Sheets

STETHOSCOPE

The present invention relates to the construction of stethoscopes and, in particular, to a stethoscope providing stereophonic detection of heart sounds.

In the conventional stethoscope, "binaural" reception is obtained by simultaneously feeding to each ear the sound produced in a single chesthead so that each ear receives the same sound. This is so even in the so-called dual stethoscope employing a bell receiver for low frequency sound and diaphragm receiver for high frequency sound. The sound produced in either mode is selectively combined in a respective chamber and fed to the ears of the user without any conversion into its natural stereo components.

Some time ago, it has been attempted to provide stereophonic reception by employing a pair of stethoscope heads arranged side by side. While such device produces two different sound patterns, the sounds were not stereophonic in that the distance between the heads provide sound from disparate points on the chest which, in the end, became confusing to the user. This type of stethoscope was a poor diagnostic tool.

Since it would be of great advantage to provide a true stereo sound to more accurately represent the actual conditions of the patient, it is the object of the present invention to provide a stethoscope providing stereophonic reception.

It is a further object of the present invention to provide a simple, inexpensive stethoscope for stereophonic reception.

These objects, together with other objects and advantages, will be apparent from the following disclosure of the present invention.

SUMMARY OF THE INVENTION

Briefly, in accordance with the present invention, a stethoscope having dual acoustic chambers is provided in which each of its acoustic chambers is divided by a wall into two equal portions each receiving the sound waves from substantially the same point. Each acoustic portion is connected by an airway passage to a separate sound tube to direct sound separately to the respective ears of the user.

In accordance with the present invention, the stethoscope chesthead comprises a spool-like body having a recess at each end forming an acoustic chamber. Each recess is divided by a wall into two equal acoustic portions. A low frequency receiving bell is associated with one of the recesses and provides sound simultaneously to each of the portions in the recess. A high frequency diaphragm assembly is associated with the other of the recesses providing sound simultaneously to each of the portions in that recess. Two pairs of air passages extend through the body, one pair communicating at one end to the respective acoustic portions in one recess chamber, the other pair communicating at one end to the respective acoustic portion in the second recess chamber. Each passage terminates at its other end in a boss in which the tubes are clustered for selective connection to a sound tube exteriorly of the body. The sound tubes are thus alternatively connectable to each pair of air passages to provide sound from each of the paired recess chambers to the user simultaneously. Upon switching from low to high frequency sensing, the sound tubes are also switched consequently allowing the user access to either set of recess chambers.

Full details of the present invention are set forth in the following description and illustrated in the accompanying drawings.

DESCRIPTION OF THE INVENTION

Figure 1:
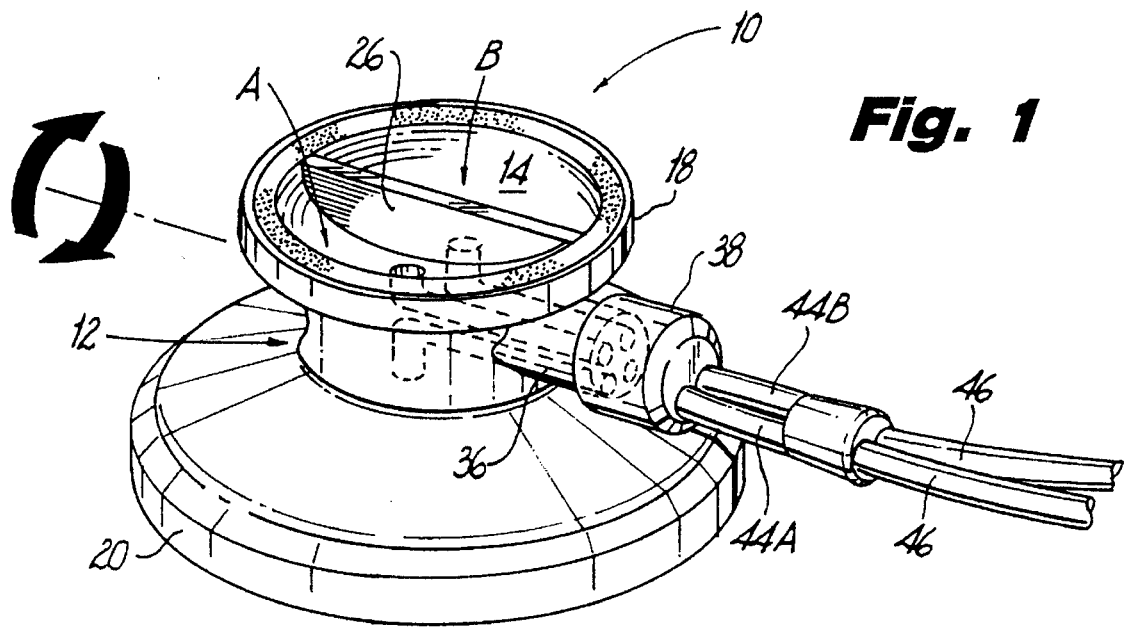
FIG. 1 is a perspective view of the stethoscope of the present invention illustrating, in broken lines, the interior air passageways.
Figure 2:
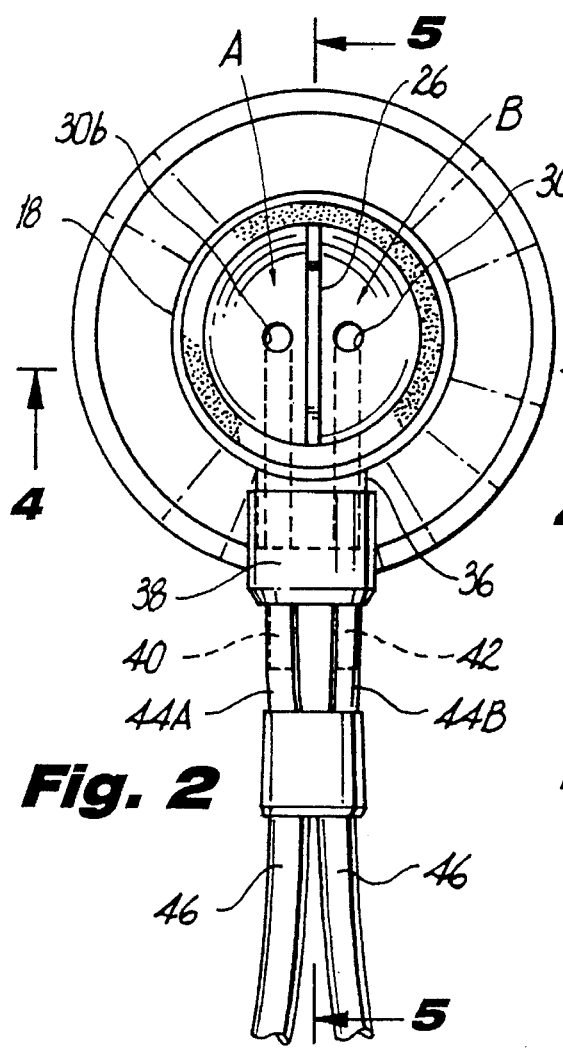
FIG. 2 is a top plan view of the stethoscope.
Figure 3:
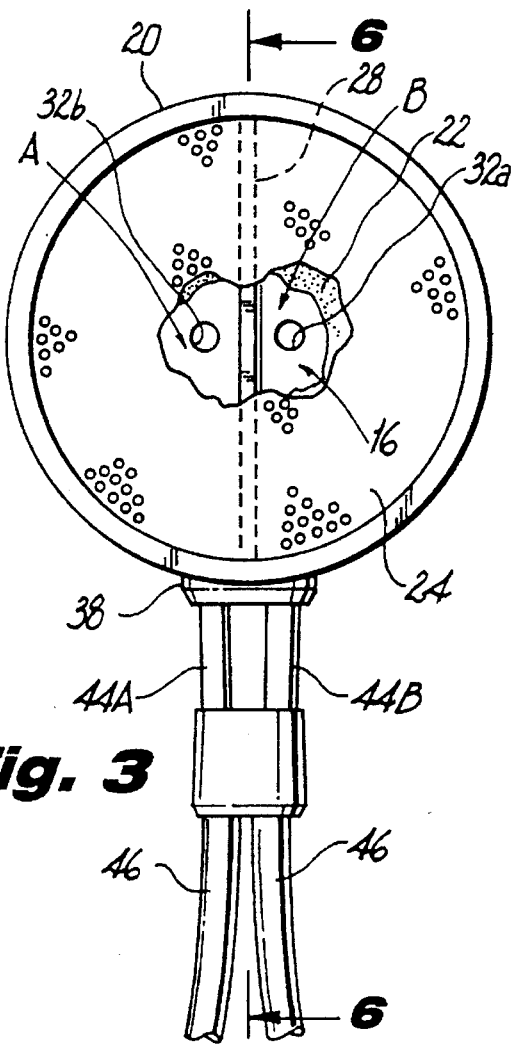
FIG. 3 is a bottom plan view of the stethoscope.
Figure 4:
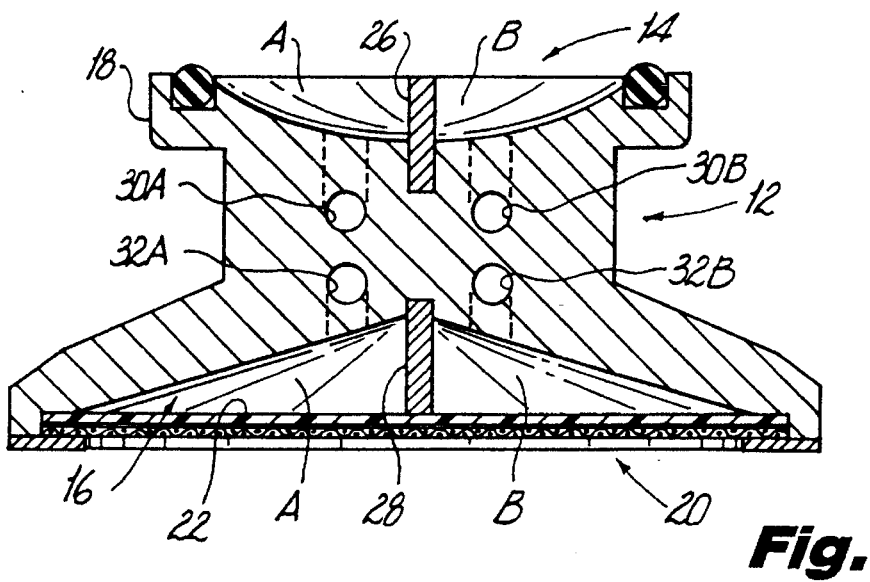
FIG. 4 is a cross-sectional view of the stethoscope taken along line 4—4 of FIG. 2.
Figure 5:
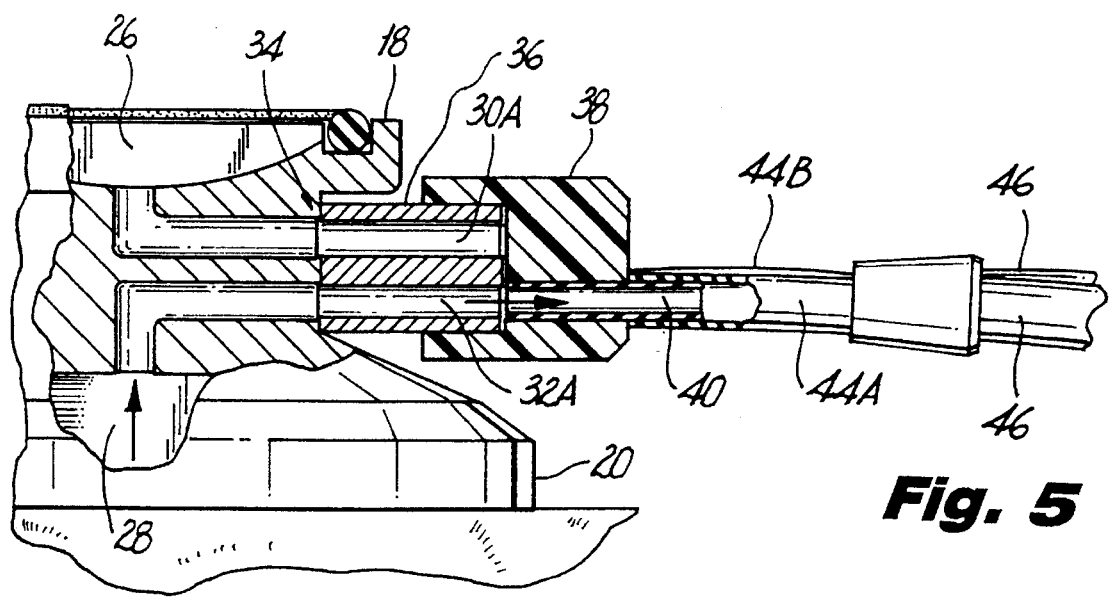
FIG. 5 is a sectional view of the stethoscope taken along line 5—5 of FIG. 2.
Figure 6:
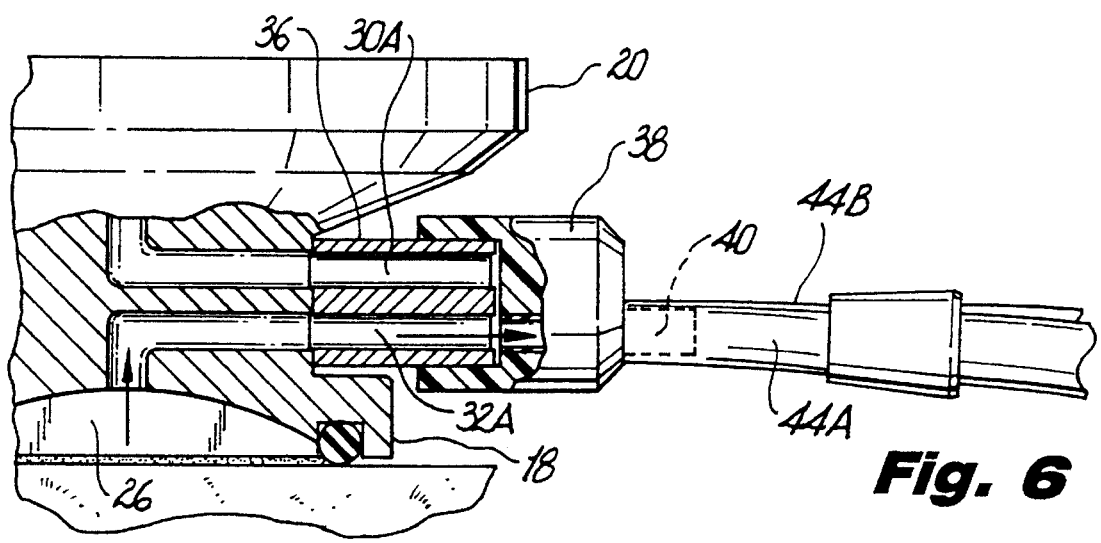
FIG. 6 is a sectional view of the stethoscope taken along line 6—6 of FIG. 3.

As seen in the figures, the present stethoscope, generally depicted by the numeral 10, comprises a solid, spool-like chesthead 12 recessed to form chambers 14 and 16 at each of its ends, respectively. The upper chamber 14 comprises a low frequency sound receiving bell assembly 18 while the lower chamber 16 is closed by a high frequency sound receiving diaphragm assembly 20. Both the bell and diaphragm assemblies 18, 20 are of conventional, well known and commercially available construction. For example, reference to the structure and parts of the Sprague-Rappaport type stethoscope can be made as if more fully set forth herein.

The bell assembly 18 may be formed by the concave cross-sectional configuration of the chamber 14 above, or it may comprise a concave bowl-like member secured over the opening of the chamber 14, the bowl-like member having at least one acoustical passage into the chamber. The high frequency diaphragm assembly 20 may include a plastic diaphragm disk 22 held on the exterior lip of the chamber 16 by a perforated cover plate 24 and O-ring separators, the diaphragm being capable of amplifying the heart sounds acoustically.

According to the present invention, each of the chambers 14 and 16 is divided into two portions, sublabelled A and B, by a diametric bulkhead or wall 26, 28, respectively. Preferably, the bulkhead or wall 26 is centered along a diameter of the chamber 14 or 16 so as to provide portions A and B of substantially equal size and configuration. Four bores 30A, 30B and 32A, 32B, extend through the solid center of the spool, each having one end in communication with a respective one of the chamber portions 14A, 14B and 16A and 16B, and having their other ends opening in a cluster 34 on the exterior cylindrical wall of the chesthead 12. Mounted over the opening cluster 34 on the exterior wall of the head 12 is a boss 36 on which is rotatably secured a switch plate 38 having embedded therein a pair of airway plug fittings 40 and 42. The fittings 40 and 42 are arranged in the switch plate 38 so that on rotation of the switch plate, the passageway fittings 40, 42 are paired in alignment with either the bores 30A, 30B or 32A, 32B to thereby selectively receive the sound from each of the chesthead chamber portions A and B of either the low frequency bell assembly 18 or the high frequency diaphragm assembly 20.

Removably attached to each of the fittings 40 and 42, respectively, are a pair of flexible sound tubes 44A and 44B at the end of each of which is secured a separate binaural tube 46 provided with the usual ear tip and which extend to fit into the user's ears.

As will be apparent from the foregoing, the present invention thus allows stereophonic reception, each ear of the user receiving predetermined acoustics from the A or B chambers of either bell assembly 18 or the diaphragm assembly 20. That is, one ear hears the A sounds and the other ear the B sounds of a given chamber 14 or 16. Then when the user reverses the chesthead, the switch plate 38 will also be renewed so that the ears now hear the separate A and B sounds of the other chamber. The independent sound detection through the paired passageways provides a more accurate stereo detection system of sound waves than that of a conventional stethoscope which collects sounds only through one common acoustic chamber having passages connected to the common chamber.

The present stethoscope is also advantageous over the discarded proposal of using two separate stethoscope heads. The present invention is simpler, smaller and substantially less expensive. It further is more accurate in its detection of the heart sounds in that each ear receives its stereo component from an acoustic chamber of the other ear. Thus, true stereo sound is received from each point of stethoscope head contact with the body.

Various modifications have been suggested herein. Other changes and modifications will be apparent to those skilled in this art. It is therefore intended that the present disclosure be taken as illustrative only and not as limiting of the invention.

What is claimed is:

1. A stethoscope comprising a head having a main body formed with a pair of acoustic chambers for receiving sound, a wall dividing each of said chambers into two equally shaped portions, a passage extending through said body from each of said chamber portions, each passage terminating exterior of said body in a boss, a cluster housed in said boss means for selectively pairing the passages from each of the portions in each chamber, and a sound tube for delivering sound separately from each portion of the associated chamber to the ears of the user, said means for selectively pairing the passages comprising a switch plate rotatably mounted on said boss, said switch plate having a pair of airway connections to which said sound tubes are connected, said pair of airway connections and said passages in said body being cooperatively arranged so that on selective rotation of said switch plate said airway connections are operatively aligned with the pair of passages from one or the other of said acoustic chambers.

2. The stethoscope according to claim 1, including a low frequency sound sensor located in one of said chambers and a high frequency sensor located in the other chamber for detecting sound in the respective chambers.

3. The stethoscope according to claim 2, wherein said low frequency sound sensor is a bell assembly and the high frequency sound sensor is a diaphragm assembly.

* * * * *